United States Patent [19]

Lafon, deceased

[11] Patent Number: 5,391,576
[45] Date of Patent: Feb. 21, 1995

[54] METHOD FOR TREATING AND PROTECTING THE CEREBRAL TISSUE AGAINST REPERCUSSIONS OF CEREBRAL ISCHAEMIA AND CEREBRAL INFARCTIONS

[75] Inventor: Louis Lafon, deceased, late of Paris, France, by Andrée Victorine Léonie Marie Lafon, Legal Representative

[73] Assignee: Laboratoire L. Lafon, Maisons Alfort, France

[21] Appl. No.: 988,271

[22] Filed: Dec. 14, 1992

[30] Foreign Application Priority Data

Dec. 13, 1991 [FR] France ................ 91 15534

[51] Int. Cl.6 .......................... A61K 31/165
[52] U.S. Cl. ................................. 514/618
[58] Field of Search ............. 514/618; 564/162

[56] References Cited

U.S. PATENT DOCUMENTS 4,177,290 12/1979 Lafon ................ 564/162
4,927,855 5/1990 Lafon ................ 514/618
5,180,745 1/1993 Lafon ................ 514/618

FOREIGN PATENT DOCUMENTS 2385693 10/1978 France ............ A61K 31/16

Primary Examiner—Raymond J. Henley, III
Assistant Examiner—K. Weddington
Attorney, Agent, or Firm—Jacobson, Price, Holman & Stern

[57] ABSTRACT

The invention relates to a method for protecting the cerebral tissue of a human against the repercussions of ischaemia which comprises administering to a patient in need thereof a therapeutically effective amount of modafinil.

5 Claims, No Drawings

METHOD FOR TREATING AND PROTECTING THE CEREBRAL TISSUE AGAINST REPERCUSSIONS OF CEREBRAL ISCHAEMIA AND CEREBRAL INFARCTIONS

The present invention relates to a new use of modafinil in therapy.

Modafinil or (benzhydryl sulfonyl) acetamide is a compound of formula

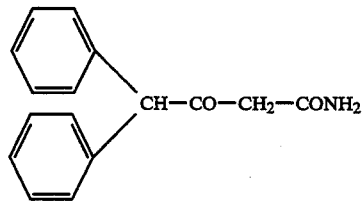

This compound and its therapeutic application as an active agent on the central nervous system have been described in Patent FR-A-2,385,693.

It has now been discovered that modafinil possesses a protective effect against the repercussions of ischaemia on cerebral tissue, which effect may be used in therapy, in particular in the treatment of cerebral infarctions and acute and chronic cerebral ischaemias.

Therefore, the present invention relates to the use of modafinil for protecting the cerebral tissue of a human against the repercussions of ischaemia and in particular for the treatment of cerebral ischaemias. More specifically, the present invention relates to the use of modafinil for the chronic treatment of stroke and for the treatment of transient ischaemic attack.

For this use, modafinil may be presented in particular in a form suitable for oral administration. Generally, the doses administered may be from 1 mg/kg to 100 mg/kg.

Results of pharmacological tests demonstrating the anti-ischaemic effects of modafinil are given below.

1. Effects of modafinil on striatal lesions produced in male Sprague-Dawley rats in the cerebral area of the neostriatum by the production of an acute local tissue ischaemia induced by in-situ injection of endothelin-1 (vasoconstrictor agent).

The experimental method has been described by K. Fuxe et al. (Endothelin-1 induced lesions in the brain as a new model of focal ischemia, Conn PM (ed) Methods in Neurosciences, Vol. 7). Briefly, the rats are anaesthetised and placed in assisted ventilation. The head of the rats is placed in a stereotaxis frame. Three elements are implanted locally in the neostriatum:

1) a needle to carry out the microinjections of endothelin-1 (ET-1);
2) a microdialysis probe to carry out microsampling for the biochemical assays of lactic acid and pyruvic acid released into the extracellular spaces, and finally
3) a Doppler laser microprobe, the purpose of which is to measure blood flow in the lesion area.

Systemic arterial blood pressure is measured peripherally with a pressure sensor.

The histopathological repercussions on the neostriatum are determined on the animal's brain removed, after sacrifice of the animals, seven days after induction of the local infarction by injection of endothelin-1. The volume of the lesion is measured by means of a computer-assisted image analyser according to the technique described by Agnati et al. (Neuroscience, 1988, 26, 461–478) and Zoli et al. (Develop. Brain Res. 1980, 51, 45–61). Anatomopathological sections are prepared with an ultramicrocryotome over the whole of the neostriatum every 100 μm with a section thickness of 4 μm. The neurons are stained with cresyl violet (Nissl staining), and the glial cells by immunochemical staining of glial fibrillary acidic protein (GFAP).

Modafinil is administered daily intraperitonealy at doses of 10, 30 and 100 mg/kg, for a period of seven days with the first injection 30 minutes before the injection of endothelin-1 at a dose of 1 μg/ml.

In addition, biochemical analyses (lactic and pyruvic acids) were performed, as well as a behaviourial study by observation of the ipsilateral rotational movements induced by intraperitoneal injection of apomorphine (1 mg/kg).

Table I shows the effect of modafinil on the tissue volume of the lesion expressed in $mm^3$. The doses of 30 and 100 mg/kg produce a dose-dependent reduction in the volume of the ischaemic lesion.

TABLE I

| Treatment (i.p.) | Dose (mg/kg) | n | Lesion volume ($mm^3$) Cresyl violet | GFAP IR |
|---|---|---|---|---|
| Solvent |  | 5 | 11.11 ± 1.45 | 18.26 ± 1.42 |
| Modafinil | 10 | 5 | 9.05 ± 0.39 | 14.18 ± 1.31 |
| Modafinil | 30 | 4 | 5.49 ± 1.09 | 9.01 ± 0.80 |
| Modafinil | 100 | 5 | 3.07 ± 0.68 | 4.46 ± 0.62 |

The anatomo- and histopathological studies show that the neurons, in particular in the immediate periphery of the area of tissue necrosis, are more numerous when compared with control animals, and display cellular trophicity comparable to the neurons of the non-ischaemic areas. Moreover, glial infiltration within and surrounding the lesion is less intense in the animals treated with modafinil.

Table II summarises the results of the blood flow measurements in the neostriatum and the peripheral measurements of systolic arterial blood pressure. These data show that modafinil has no effect on blood flow. Thus, the anti-ischaemic effect of modafinil is independent of an action on local tissue perfusion and is not linked to a haemodynamic effect.

TABLE II

| Treatment i.p | Dose (mg/kg) | Time after injection of ET-1 % variation | | | | | | |
|---|---|---|---|---|---|---|---|---|
| | | 10 | 20 | 40 | 60 | 80 | 100 | 120 |
| Blood flow | | | | | | | | |
| Solvent (n = 6) |  | −14.6 ± 3.9 | −52.0 ± 15.1 | −44.1 ± 12.2 | −35.9 ± 5.9 | −34.2 ± 5.9 | −32.7 ± 5.3 | −32.7 ± 5.5 |
| Modafinil (n = 6) | 100 | −31.8 ± 15.5 | −38.6 ± 11.5 | −36.5 ± 9.2 | −38.2 ± 12.3 | −30.0 ± 11.8 | −21.2 ± 12.5 | −18.5 ± 13.8 |
| Modafinil (n = 5) | 30 | −13.5 ± 14.1 | −28.5 ± 19.4 | −31.8 ± 13.4 | −42.3 ± 15.8 | −39.5 ± 12.8 | −31.3 ± 12.6 | −27.6 ± 12.9 |
| Modafinil (n = 5) | 10 | −26.3 ± 18.6 | −40.4 ± 15.5 | −43.4 ± 14.9 | −43.8 ± 12.4 | −38.9 ± 14.6 | −32.5 ± 16.2 | −31.7 ± 16.2 |

TABLE II-continued

| | | Time after injection of ET-1 % variation | | | | | | |
|---|---|---|---|---|---|---|---|---|
| Treatment i.p | Dose (mg/kg) | 10 | 20 | 40 | 60 | 80 | 100 | 120 |
| Arterial blood pressure | | | | | | | | |
| Solvent (n = 6) | | 0.8 ± 3.2 | −0.7 ± 3.2 | 0.3 ± 2.3 | −0.4 ± 2.7 | −3.0 ± 2.2 | −0.3 ± 2.0 | −1.2 ± 1.9 |
| Modafinil (n = 6) | 100 | −0.2 ± 2.4 | −1.7 ± 2.4 | 1.5 ± 1.5 | −2.9 ± 1.1 | 0.5 ± 1.9 | 0.5 ± 2.4 | −0.5 ± 2.6 |
| Modafinil (n = 5) | 30 | −0.4 ± 1.7 | −0.4 ± 2.4 | −0.3 ± 2.1 | −1.5 ± 1.2 | −2.1 ± 3.1 | −0.5 ± 2.2 | −1.2 ± 3.1 |
| Modafinil (n = 5) | 10 | 0.8 ± 1.6 | 5.3 ± 4.5 | 4.3 ± 3.8 | −0.8 ± 1.9 | 1.2 ± 2.6 | 2.1 ± 2.1 | −0.4 ± 1.8 |

The biochemical data are summarised in Table III. Modafinil brings about a dose-dependent reduction in the endothelin-1-induced increase in the release of lactic acid into the extracellular spaces. The extracellular pyruvic acid concentration is not modified by modafinil.

TABLE III

| | | | Initial value | Increase | | Decrease | |
|---|---|---|---|---|---|---|---|
| Treatment | Dose | n | (mM) | Peak* (%) | AUC** | Peak* (%) | AUC** |
| | | | | Lactate | | | |
| Solvent | | 6 | 257.7 ± 64.4 | 279.5 ± 59.9 | 54748 ± 11588 | | |
| Modafinil | 10 | 5 | 250.6 ± 76.4 | 264.3 ± 105.6 | 45609 ± 8037 | | |
| Modafinil | 30 | 5 | 254.7 ± 77.0 | 219.0 ± 66.3 | 32314 ± 9057 | | |
| Modafinil | 100 | 6 | 265.5 ± 77.5 | 137.0 ± 45.3 | 20147 ± 4992 | | |
| | | | | Pyruvate | | | |
| Solvent | | 6 | 10.4 ± 2.4 | 29.7 ± 7.7 | 220.7 ± 154.5 | −30.6 ± 10.7 | −209.1 ± 99.0 |
| Modafinil | 10 | 5 | 9.8 ± 1.4 | 29.5 ± 13.2 | 106.6 ± 51.0 | −35.2 ± 11.3 | −196.3 ± 82.9 |
| Modafinil | 30 | 5 | 10.7 ± 2.5 | 35.0 ± 16.0 | 80.0 ± 34.0 | −35.9 ± 5.0 | −277.7 ± 142.7 |
| Modafinil | 100 | 6 | 10.2 ± 2.6 | 13.0 ± 8.2 | 99.0 ± 90.1 | −24.2 ± 6.6 | −101.4 ± 29.9 |

*Peak = maximum value measured
**AUC = area under the curve

The reduction in the lactic acid concentration in the extracellular spaces within the lesion area, whereas blood perfusion is reduced, suggests that modafinil is responsible for a beneficial effect on the utilisation of available oxygen, favourable to the functions and to the neuronal trophicity.

2. Effects of modafinil treatment on the apomorphine-induced ipsilateral rotational behaviour in the rat with a unilateral endothelin-1 (ET-1) induced lesion in the neostratium.

The behaviour was tested on day 6 after the ET-1 injection. One mg/kg of the non selective dopamine receptor agonist apomorphine hydrochloride was injected subcutaneously (s.c.) in the neck 1 hour after the daily modafinil administration. The apomorphine-induced ipsilateral rotational behavior was measured in a rotometer (Ungerstedt and Arbuthnott, 1970). The rotational counts (360° turns) were recorded at 5-min. intervals for a total period of 60 minutes. In experiments on unilaterally 6-hydroxy dopamine lesioned rats in the substantia nigra (4 weeks earlier) modafinil in dose of 30–100 mg/kg has been shown not to change apomorphine and amphetamine induced rotation behaviour when given 30 minutes before the dopaminergic drugs.

The area values (overall effects) formed by the curves with the base line are expressed as mean ±SEM in arbitrary units. The peak values (maximal responses) are expressed as rotation counts (360° turns/5 minutes). Statistical analysis was performed with the non-parametric test, treatments vs control (* P<0.05) and the Jonckheere-Terpstra test (JT) for dose-related effects (significance written in the table).

The data are summarized in Table IV.

TABLE IV

| Treatment | Dose (mg/kg) | n | Ipsilateral rotation Peak | Area |
|---|---|---|---|---|
| Solvent | | 5 | 57.2 ± 3.3 | 1701.0 ± 34.2 |
| Modafinil | 10 | 5 | 41.4 ± 7.6 * | 1237.5 ± 325.0 * |
| Modafinil | 30 | 5 | 26.2 ± 0.8 * | 706.0 ± 61.4 * |
| Modafinil | 100 | 5 | 11.2 ± 2.4 | 276.0 ± 87.9 |

JT:P < 0.01    JT:P = 0.01

The psychobehavioural studies by measurement of the apomorphine-induced ipsilateral rotational movements show that modafinil brings about a dose-dependent inhibition of the ipsilateral rotational movements in rats having an endothelin-1-induced striatal lesion. This inhibition is total at a dose of 100 mg/kg.

The histo/anatomopathological, biochemical and psychobehavioural results are concordant, and demonstrate that modafinil exerts an anti-ischaemic effect by a direct or indirect action on neuronal vitality, trophicity and functions, as well as by a reduction in the glial reaction within and surrounding the lesion.

3. Studies on the photochemically induced cerebral infarct:

These studies use the photochemical stroke model disclosed by Marc De RYCK et al., Stroke 20, IV, 1383.

Studies on hindlimb placing errors:

The effects of a 6-day treatment with modafinil on the number of placing errors of the contralateral hindlimb on an elevated beam after photochemically induced thrombosis of the sensory-motor cortex in the Sprague-Dawley rat are shown in Table V.

TABLE V

| Hindlimb placing errors (controlateral side) | | | |
|---|---|---|---|
| Rat | Control | Rat | Modafinil (100 mg/kg) |
| 1 | 9 | 15 | 8 |
| 2 | 9 | 16 | 10 |
| 3 | 14 | 17 | 10 |

TABLE V-continued

| Hindlimb placing errors (controlateral side) | | | |
|---|---|---|---|
| Rat | Control | Rat | Modafinil (100 mg/kg) |
| 4 | 9 | 18 | 7 |
| 5 | 9 | 19 | 8 |
| 6 | 16 | 20 | 8 |
| 7 | 12 | 21 | 7 |
| 8 | 11 | 22 | 5 |
| 9 | 9 | 23 | 7 |
| 10 | 7 | 24 | 8 |
| 11 | 10 | 25 | 5 |
| 12 | 11 | 26 | 2 |
| 13 | 10 | 27 | 7 |
| 14 | 6 | | 7(5–8)* |
| | 9.5(9–11) | | |

*$p < 0.025$.

As seen in Table V, modafinil treatment in the Sprague-Dawley rat in doses of 10–100 mg/kg produces a dose-related reduction in the number of hindlimb placing errors on the contralateral side on day 7 after a daily modafinil treatment. The action becomes significant at 100 mg/kg of modafinil.

These results on the hindlimb placing errors suggest that the 6-day modafinil treatment can reduce the Dyskynesis phenomenon (secondary changes in other brain areas) occuring after stroke.

Studies on rotational behaviour:

The effects of a 6-day treatment with modafinil on the apomorphine-induced contralateral rotational behaviour in Sprague-Dowley rats with photochemically induced thrombosis in the sensory-motor cortex are shown in Table VI.

TABLE VI

| | SOLVENT | | MODAFINIL (100 mg/kg) | |
|---|---|---|---|---|
| Rat | Total turns | Peak | Total turns | Peak |
| 1 | 79 | 2.4 | 145 | 4.6 |
| 2 | 80 | 2.5 | 136 | 4.9 |
| 3 | 123 | 3.3 | 201 | 6.0 |
| 4 | 19 | 0.5 | 26 | 1.2 |
| 5 | 98 | 3.0 | 114 | 4.0 |
| 6 | 56 | 2.1 | 55 | 1.9 |
| 7 | 84 | 2.6 | 142 | 5.5 |
| 8 | 64 | 2.3 | 47 | 1.7 |
| 9 | 69 | 2.2 | 86 | 2.4 |
| 10 | 47 | 1.0 | 106 | 2.5 |
| 11 | 48 | 1.8 | 54 | 2.3 |
| 12 | 72 | 2.4 | 160 | 4.9 |
| 13 | 14 | 1.7 | 62 | 2.0 |
| 14 | 18 | 1.4 | 150 | 4.1 |
| | 6 ± 8.4 | 2.1 ± 0.2 | 106 ± 13.9** | 3.4 ± 4.2** |

**$p < 0.01$.

The effects of a 6-day treatment with various doses of Modafinil on the apomorphine induced contralateral rotational behaviour in Sprague-Dowley rats with photochemically induced thrombosis in the sensory-motor cortex are shown in Table VII.

TABLE VII

| Treatment | Dose mg/kg | Contralateral rotational behaviour | |
|---|---|---|---|
| | | Total turns | Peak (turns/min/rat) |
| Solvent | | 44.6 ± 10.0 | 1.7 ± 0.2 |
| Modafinil | 10 | 44.3 ± 12.5 | 1.7 ± 0.3 |
| Modafinil | 30 | 91.6 ± 20.7 | 2.8 ± 0.6 |
| Modafinil | 100 | 102.9 ± 17.9 | 3.0 ± 0.5 |
| Joncheere-Terpstra test | | $p < 0.01$ | $p < 0.05$ |

The findings that the 6-day modafinil treatment could in a dose-related manner enhance contralateral rotational behaviour induced by apomorphine in the rats with focal ischaemia in the sensory-motor cortex are of substantial interest. The findings indicate that upon removal of many of the corticostriatal glutamate fibres by the focal ischaemia in the cortex, the 6-day modafinil treatment appears to sensitize the striatal nerve cells to the dopaminergic (DAergic) activation by apomorphine leading inter alia to a prolongation of the action of DA receptor activation.

Taken together, the results obtained in the photochemical stroke model indicate that the 6-day modafinil treatment may reduce the diaschisis phenomenon and have the potential to improve motor recovery after a neocortical infarct without altering the size of the infarct volume or the astroglia and the microglia reaction as evaluated mainly on day 7 after the lesion. Nevertheless, after 4 hours, a morphological protective action may be present by modafinil (100 mg/kg).

What is claimed is:

1. A method for protecting the cerebral tissue of a human against the repercussions of ischaemia which comprises administering to a patient in need thereof a therapeutically effective amount of modafinil.

2. A method for the treatment of cerebral infarctions which comprises administering to a patient in need thereof a therapeutically effective amount of modafinil.

3. A method for the treatment of cerebral ischaemia which comprises administering to a patient in need thereof a therapeutically effective amount of modafinil.

4. A method for the chronic treatment of stroke which comprises administering to a patient in need thereof a therapeutically effective amount of modafinil.

5. A method for the treatment of transient ischaemia attack which comprises administering to a patient in need thereof a therapeutically effective amount of modafinil.

* * * * *